United States Patent [19]

Takeda et al.

[11] 4,331,034

[45] May 25, 1982

[54] ULTRASONIC PROBING APPARATUS

[75] Inventors: Hiroyuki Takeda, Hiroshima; Ichio Iseki, Sendai; Katsumi Kawai, Tokyo; Hiroyuki Okajima, Nagoya; Sigeru Kajiyama, Hitachi; Sakae Sugiyama, Tokaimura; Kimio Kanda, Hitachi, all of Japan

[73] Assignees: The Chugoku Electric Power Co., Inc.; Tohoku Electric Power Co., Inc.; The Tokyo Electric Power Co., Inc.; The Chubu Electric Power Co., Inc.; Hitachi, Ltd., all of Japan

[21] Appl. No.: 63,775

[22] Filed: Aug. 6, 1979

[30] Foreign Application Priority Data

Apr. 9, 1979 [JP] Japan ............................ 54-42068

[51] Int. Cl.³ ............................................. G01K 29/04
[52] U.S. Cl. ........................................ 73/637; 73/592
[58] Field of Search .................. 73/622, 638, 640, 635, 73/637, 640, 625, 636, 639, 592

[56] References Cited

U.S. PATENT DOCUMENTS

| | | | |
|---|---|---|---|
| 2,799,157 | 7/1957 | Pohlman | 73/635 |
| 3,248,933 | 5/1966 | Stebbins | 73/640 |
| 3,715,914 | 2/1973 | Gross et al. | 73/622 |
| 3,863,496 | 2/1975 | Himamatsu et al. | 73/640 |
| 3,921,440 | 11/1975 | Toth | 73/622 |

FOREIGN PATENT DOCUMENTS 52-108874 3/1977 Japan .................. 73/622 X

*Primary Examiner*—Daniel M. Yasich
*Attorney, Agent, or Firm*—Thomas E. Beall, Jr.

[57] ABSTRACT

An annular guide rail is detachably mounted in enclosing relation around a tubular member of piping to be probed for any flaws that might be present therein, and a flaw detecting unit, a circumferentially driving unit and an axially driving unit are movably arranged on the annular guide rail and interconnected by connecting means. The flaw detecting means includes an arm movable axially of the tubular member and supporting ultrasonic flaw detecting means. The circumferentially driving unit includes first driving means for moving the flaw detecting unit, circumferentially driving unit and axially driving unit circumferentially along the guide rail. The axially driving unit includes second driving means for moving the arm axially of the tubular member. A transmission mechanism is provided for transmitting the operation of the second driving means to the arm.

8 Claims, 8 Drawing Figures

4,331,034

ULTRASONIC PROBING APPARATUS

BACKGROUND OF THE INVENTION

This invention relates to an ultrasonic probing apparatus, and more particularly to an ultrasonic probing apparatus of the type for probing tubular members of piping to detect any flaws, which is suitable for carrying out testing in those portions of the piping in which the spacing between the tubular members is small.

In a nuclear power plant, ultrasonic probing of the tubular members of its complex system of pipes is carried out to ascertain the flawlessness of the piping in maintenance and inspection immediately after the nuclear power plant is built and also after the plant is shut down. In carrying out maintenance and inspection following the shutdown of the nuclear power plant, the objects to be inspected exist in radioactive atmosphere, and thus there arises the need to use a remotely controlled automatic ultrasonic probing apparatus (hereinafter referred to simply as an ultrasonic probing apparatus) to eliminate the danger of exposing the operator for effecting ultrasonic probing to radiation. Programs are now under way in various quarters for developing ultrasonic probing apparatus. In ultrasonic probing apparatus, severe restrictions are placed on their weight and bulk and a high degree of precision is required in carrying out tests.

In a nuclear power plant, pipes of complicated pipe system are arranged close together and the spacing between the pipes is naturally small. Therefore, one of the important problems that should be solved for ultrasonic probing apparatus is how to reduce the height of the apparatus sufficiently to avoid the collision of the apparatus against the adjacent pipe in moving the apparatus circumferentially of the pipe to be probed for any flaws that might be present therein. If the ultrasonic probing apparatus had a large height, movement of the apparatus circumferentially of a pipe would be interfered with, thereby making it impossible to effect ultrasonic probing of pipes to detect flaws.

One example of ultrasonic probing apparatus is disclosed in U.S. Pat. No. 3,921,440 in which a guide rail is mounted around a pipe to be tested, and a driving member is arranged on the guide rail for movement therealong. An arm having a probing means at its forward end is mounted on the driving member for movement along the axis of the pipe. The driving member has also mounted thereon a swinging mechanism for moving the probing means in swinging movement in a horizontal plane. The aforesaid parts constitute a driving unit of the ultrasonic probing apparatus. The probing means is provided with an angle varying mechanism for varying the angle of incidence of ultrasonic sound waves incident on the surface to be probed. The driving member is provided with a circumferentially driving mechanism for moving the probing means circumferentially of the pipe to be probed and an axially driving mechanism for moving the probing means axially of the pipe, as well as the swinging mechanism for the probing means. Moreover, the angle varying mechanism is mounted in the probing means, so that the driving means has a very great height. Thus, in this ultrasonic probing mechanism, difficulties would be encountered in moving the probing means circumferentially of the pipe to be probed.

SUMMARY OF THE INVENTION

This invention has as its object the provision of an ultrasonic probing apparatus which has a very small height as compared with conventional ultrasonic probing apparatus.

The outstanding characteristics of the invention are that an annular guide rail is detachably mounted around a pipe to be probed in enclosing relation, and a flaw deteching unit, a circumferentially driving unit and an axially driving unit are movably arranged on the annular guide rail and interconnected by connecting means. The flaw detecting unit includes ultrasonic probing means and an arm movable axially of the pipe. The circumferentially driving unit includes circumferentially driving means for moving the circumferentially driving unit circumferentially of the annular guide rail. The axially driving unit includes axially driving means operative to move the arm axially of the pipe. There is provided a transmission mechanism for transmitting the operation of the axially driving means to the arm. By arranging the aforesaid various units of the ultrasonic probing apparatus in scattered relation around a pipe to be probed, it is possible to markedly reduce the height of the apparatus, so that ultrasonic probing of the entire circumference of the pipe can be effected without any trouble even if the pipes are located close together.

DESCRIPTION OF THE PREFERRED EMBODIMENTS

Figure 1:
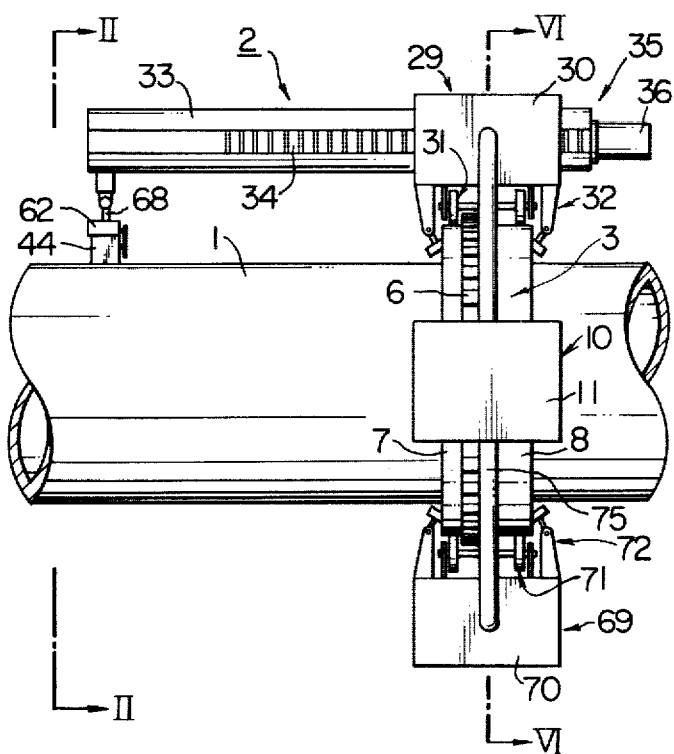
FIG. 1 is a side view of the ultrasonic probing apparatus comprising a preferred embodiment of the invention, showing the apparatus as mounted around a pipe.

A preferred embodiment of the ultrasonic probing apparatus in conformity with the invention will now be described by referring to FIGS. 1 and 2. The ultrasonic probing apparatus generally designated by the numeral 2 comprises a guide rail 3, a circumferentially driving unit 10, a flaw detecting unit 29 and an axially driving unit 69. The guide rail 3 includes two frames 4 and 5. Although not shown, the frames 4 and 5 are connected, at one end thereof, to each other by means of a hinge used with the track module shown in U.S. Pat. No. 3,921,440, and, although not shown, are provided, at the other end thereof, with a latch used with the track module shown in the U.S. patent referred to hereinabove. By opening the latch, one end (A in FIG. 2) of the frames 4 and 5 can be hingedly opened and mounting of the guide rail 3 around a pipe 1 can be facilitated. Located substantially in the central portion of the outer peripheries of the frames 4 and 5 is a rack 6 which is interposed between planar surface portions 7 and 8 of the outer peripheries of the frames 4 and 5 disposed at a lower level than the upper surface of the rack 6. The aforesaid hinge is mounted in a recess formed in the planar surface portion 8 of a larger width of the frames 4 and 5 so as to avoid interference with the movement of wheels of trucks subsequently to be described. The aforesaid latch is mounted on a lateral side 9 of the frames 4 and 5 (See FIG. 3). Attached to the inner peripheries of the frames 4 and 5 are space holders 94 for fixing in place the guide rail 3 concentrically with the pipe 1 when the former is arranged in its position around the later.

Figure 3:
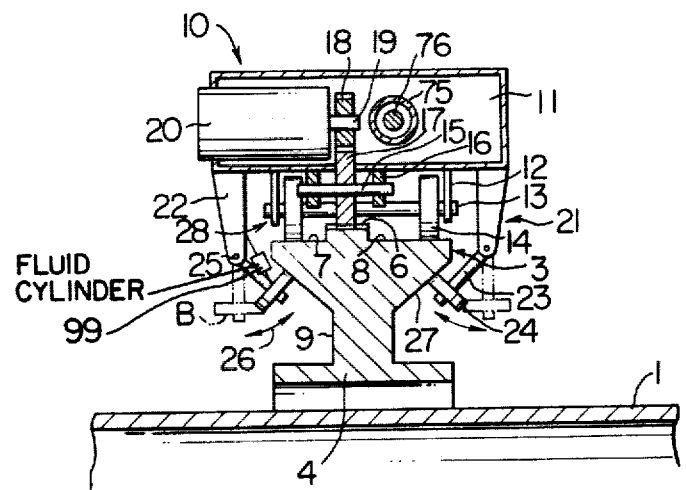
FIG. 3 is a sectional view taken along the line III—III in FIG. 2.

As shown in detail in FIG. 3, the circumferentially driving unit 10 includes a truck 11 having attached to its underside a pair of support members 12 supporting an axle 13. The axle 13 has a wheel 14 secured to each end thereof. The support members 12, axle 13 and wheels 14 constitute guide means 28. Attached to the underside of the truck 11 is a pair of support members 16 supporting a rotary shaft 15 which in turn supports a gear 17. A motor 20 is mounted within the truck 11 and has connected thereto a rotary shaft 19 supporting a gear 18 which is in meshing engagement with gear 17. The truck 11 has mounted in each of the front and rear thereof a pair of rolling preventing mechanisms 21 each comprising a fixed member 22, an opening and closing member 23 and a wheel 24. The fixed member 22 is attached to the underside of the truck 11, and the opening and closing member 23 having the wheel 24 connected to its lower end is mounted through a pivot pin 25 on the fixed member 22 for opening and closing movement. Opening and closing initiating means 99 is connected to the fixed member 22 to open and close the opening and closing member 23 in the direction of an arrow 26. The two pairs of rolling preventing mechanisms 21 are juxtaposed against each other with wheels 14, gear 17, etc., being interposed therebetween. The opening and closing initiating means 99 may comprise pneumatic pistons utilizing pneumatic pressure, screw mechanisms rotated by manipulating a handle, etc. When the circumferentially driving unit 10 is arranged on the guide rail 3, the wheels 14 are in contact with the planar surface portions 7 and 8 respectively, and gear 17 is in meshing engagement with the rack 6. When the circumferentially driving unit 10 is arranged on the guide rail 3, the opening and closing members 23 are each located in a position B shown in broken lines in FIG. 3. By rendering the opening and closing initiating means 99 operative, the opening and closing members 23 are each brought to a closed position as shown in solid lines and the wheels 24 are brought into contact with inclined surfaces 27 of the frame 4. By closing the opening and closing members 23 of the two pairs of rolling movement preventing mechanisms 21 juxtaposed against each other, it is possible to prevent the rolling movement of the truck 11.

Figure 4:
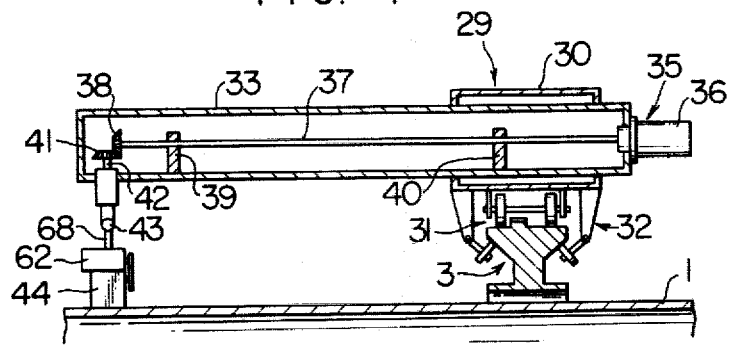
FIG. 4 is a sectional view taken along the line IV—IV in FIG. 2.

Referring to FIG. 4, the flaw detecting unit 29 includes a truck 30, an arm 33, a probing means swinging mechanism 35, probing means 44 and a probing means angle varying mechanism 62. Guide means 31 and two pairs of rolling preventing mechanisms 32 are attached to the underside of the truck 30. The guide means 31 and rolling preventing mechanisms 32 are of the same construction as guide means 28 and rolling preventing mechanisms 21 respectively. The arm 33 is connected to the truck 30 and extends therethrough for sliding movement. A rack 34 is mounted on one lateral side of the arm 33, as shown in FIG. 1.

The probing means swinging mechanism 35 is attached to the arm 33 and shown in detail in FIG. 4. A motor 36 is mounted at one end of the arm 33, and a rotary shaft 37 supporting a bevel gear 38 at one end thereof and connected to the motor 36 at the other end thereof is arranged within the arm 33 to extend longitudinally thereof and supported by support members 39 and 40 arranged within the arm 33. A bearing, not shown, is mounted on each of the support members 39 and 40 for journalling the rotary shaft 37. Extending through the arm 33 at right angles thereto is a rotary shaft 42 supporting a bevel gear 41 at one end thereof which is disposed within the arm 33, the bevel gear 41 being in meshing engagement with the bevel gear 38 supported by the rotary shaft 37 within the arm 33. A ball joint 43 is connected to the other end of the rotary shaft 42 disposed outside the arm 33.

Figure 5:
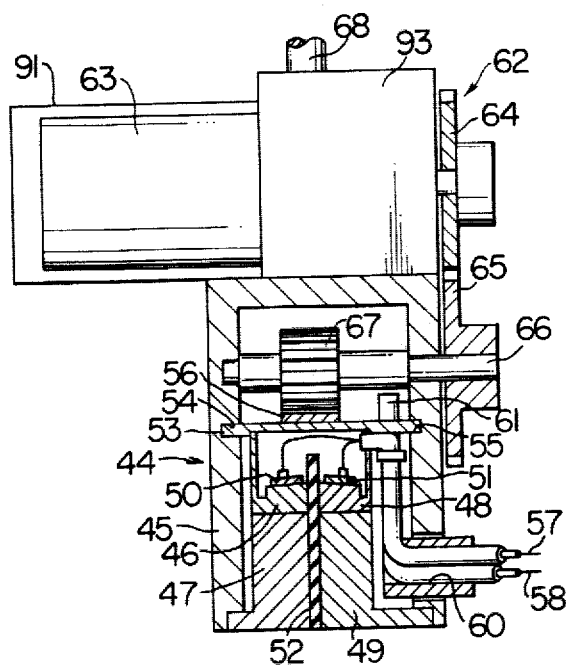
FIG. 5 is a vertical sectional view of the ultrasonic probing means.
Figure 7:
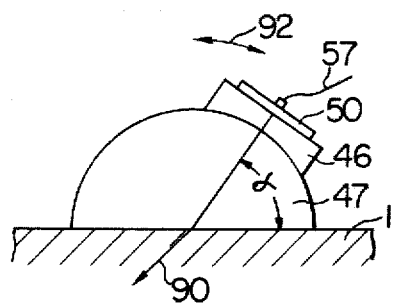
FIG. 7 is a view in explanation of the movement of the transmitter movable member of the ultrasonic probing means and the manner in which ultrasonic sound waves are transmitted.

FIG. 5 shows probing means 44 and probing means angle varying mechanism 62 of the flaw detecting unit 29. The probing means 44 comprises a casing 45, and a transmitter movable member 46, a transmitter fixed member 47, a receiver movable member 48 and a receiver fixed member 49 housed in the casing 45. The transmitter fixed member 47 and receiver fixed member 49 are fixed to the lower portion of the casing 45. The transmitter fixed member 47 is semi-circular in shape as shown in FIG. 7. The receiver fixed member 49 is of the same shape, and the center axis of the transmitter fixed member 47 is aligned with the center axis of the receiver fixed member 49. The transmitter movable member 46 and receiver movable member 48 are arranged in contact with the upper surfaces of the transmitter fixed member 47 and the receiver fixed member 49 respectively. An ultrasonic sound wave transmitter 50 and an ultrasonic sound wave receiver 51 are mounted on the upper surface of the transmitter movable member 46 and the receiver movable member 48 respectively. A sound intercepting member 52 attached to the casing 45 separates the transmitter movable member 46 and transmitter fixed member 47 from the receiver movable member 48 and receiver fixed member 49. The transmitter movable member 46 and receiver movable member 48 are secured to a guide plate 53 having opposite end portions received in arcuate guide grooves 54 and 55 respectively which are concentric with the center axes of the transmitter fixed member 47 and receiver fixed member 49 and formed on inner surfaces of the casing 45. A rack 56 is mounted on the upper surface of the guide plate 53. Cables 57 and 58 are connected to the ultrasonic sound wave transmitter 50 and ultrasonic sound wave receiver 51 respectively, and drawn to outside, in a bundle, through an opening 60 formed in the casing 45. A clamping member 61 forms the cables 57 and 58 into a bundle.

The probing means angle varying mechanism 62 comprises a motor 63, a gear box 93, gears 64, 65 and 67 and a rotary shaft 66. The motor 63 and gear box 93 are secured to the upper surface of the casing 45. Gear 64 is mounted on a speed reducing means connected to an outer shaft of the motor 63 and housed in the gear box 93. The rotary shaft 66 is inserted in the casing 45 and supports a gear 67 on a portion thereof within the casing 45 and a gear 65 on a portion thereof outside the casing 45. Gears 65 and 64 and gear 67 and rack 56 are in meshing engagement with each other. A shaft 68 is attached to the upper surface of the gear box 93 and in engagement, at its upper end, with the ball joint 43 as shown in FIG. 4.

Figure 6:
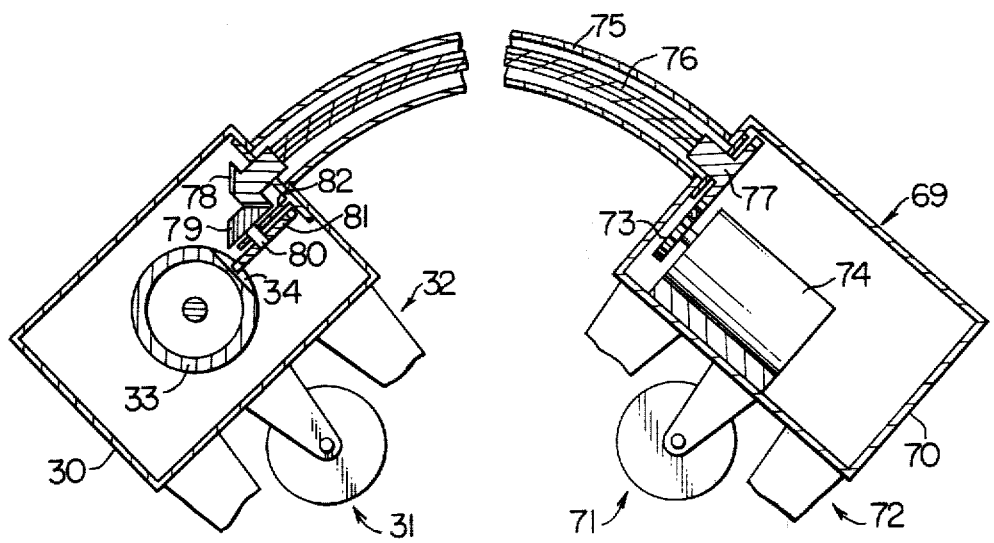
FIG. 6 is a fragmentary sectional view on the line VI—VI in FIG. 1.

Referring to FIG. 6, the axially driving unit 69 includes a truck 70. Guide means 71 and rolling preventing mechanisms 72 of the same construction as the guide means 28 and rolling preventing mechanisms 21 respectively are attached to the underside of the truck 70. A motor 74 supporting a gear 73 at its output shaft is mounted within the truck 70, and a mounting fixture 88 formed with an aperture 89 is connected to one end of the truck 70 as shown in FIG. 2.

The trucks 70, 11 and 30 are connected together in the indicated order by a connecting pipe 75 which extends through the truck 11 and is secured at opposite ends thereof to the trucks 70 and 30 respectively. A rotary shaft 76 extends through the connecting pipe 75 as shown in FIG. 6. By mounting the rotary shaft 76 within the connecting pipe 75, it is possible to simplify the construction of the ultrasonic probing apparatus 2. The rotary shaft 76 is formed as a spring or other resilient member. A gear 77 is connected to one end of rotary shaft 76 and a bevel gear 78 is connected to the other end thereof, the gear 77 being in meshing engagement with gear 73. A rotary shaft 80 is supported by a support member 82 attached to the truck 30 and has a bevel gear 79 and a pinion 81 connected to opposite ends thereof respectively. The bevel gear 79 is in meshing engagement with bevel gear 78 and the pinion 81 is in meshing engagement with rack 34.

Figure 2:
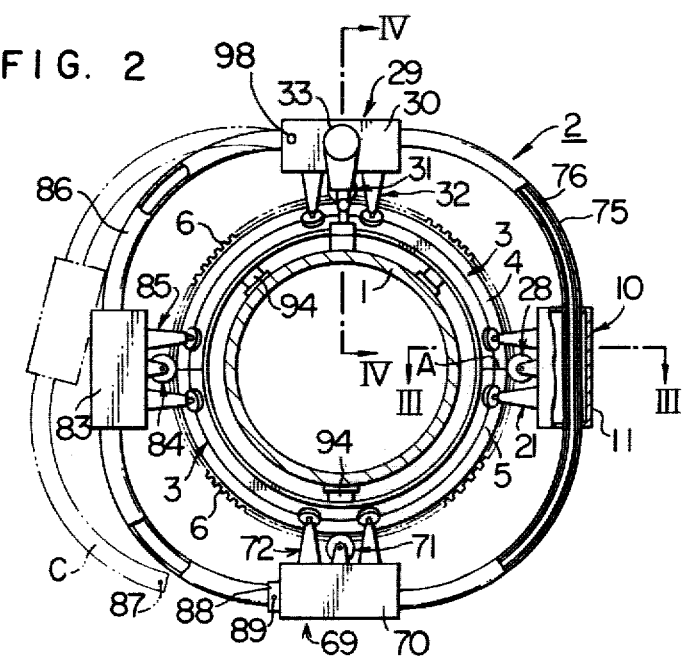
FIG. 2 is a sectional view taken along the line II—II in FIG. 1.

Referring to FIG. 2, a truck 83 is arranged on the annular guide rail 3 in a position diametrically opposed to that of truck 11. The truck 83 has attached to its underside guide means 84 and rolling preventing mechanisms 85 of the same construction as the guide means 28 and rolling preventing mechanisms 21 respectively. A connecting pipe 86 extends through the truck 83, and is pivotally connected at one end thereof to the truck 30 through a pin 98 and formed with an aperture 87 at the other end thereof. Due to the pivotal connection of pin 98, the connecting pipe 86 may swing from its full line position to its dotted line position C in FIG. 2. A pin extends through the aperture 89 of mounting fixture 88 into aperture 87 to hold the connecting pipe 86 in its full line position. When arranged on the annular guide rail 3, the trucks 30, 11, 70 and 83 are disposed at a 90 degree spacing from one another. This arrangement enables the weights of all the trucks to be evenly distributed on the guide rail 3.

As aforesaid assembly of the apparatus on a pipe is as follows. The guide rail 3 is mounted around the pipe 1 to be ultrasonically probed for any flaws which might be present therein. After the connecting pipe 86 is released from the truck 70 the pipe 86 with truck 83 is swung clockwise about pivot pin 98 to an open position, and then as indicated by C in FIG. 2, the circumferentially driving unit 10, flaw detecting unit 29, axially driving unit 69 and truck 83 are arranged on the annular guide rail 3. One end of the connecting pipe 86 is inserted into the mounting fixture 88 by rotating the pipe 83 counterclockwise about pivot pin 98 and a pin is inserted in the apertures 87 and 89, thereby mounting the aforementioned units and truck 83 on the annular guide rail 3. It is to be understood that the opening and closing member of each rolling preventing mechanism for each truck is closed at this time, for example, the initiating means 99, for example a fluid cylinder, is actuated to move the members 23 from their dotted line position B to their full line position as shown in FIG. 3.

Upon the motor 20 of the circumferentially driving unit 10 being rendered operative, gears 18 and 17 rotate and cause truck 11 and other three trucks 30, 70 and 83, connected to truck 11 by the connecting means comprising the connecting pipes 75 and 86, to move along the annular guide rail 3. The probing means 44 moves circumferentially of the pipe 1 while being maintained in contact with the surface thereof, so as to carry out ultrasonic probing of the pipe 1 circumferentially thereof to detect any flaws which might be present therein. As shown in FIG. 7, ultrasonic sound waves 90 are transmitted from the ultrasonic sound wave transmitter 50 and pass through the transmitter movable member 46 and transmitter fixed member 47 before reaching the pipe 1. The ultrasonic sound waves returning from the pipe 1 pass through the receiver fixed member 49 and receiver movable member 48 before being received by the ultrasonic sound wave receiver 51. The sound intercepting member 52 acoustically separates the transmitter movable member 46 from the receiver movable member 48 and the transmitter fixed member 47 from the receiver fixed member 49.

The movement of the probing means 44 axially of the pipe 1 is effected as follows. The driving means or motor 74 of the axially driving unit 69 (FIG. 6) is rendered operative and the rotation of motor 74 is transmitted, through transmission means comprising gears 73 and 77, rotary shaft 76, bevel gears 78 and 79 and rotary shaft 80, to the pinion 81 of the flaw detecting unit 29. The rotation of pinion 81 moves the arm 33 axially of the pipe 1 through the rack 34 in meshing engagement with the pinion 81 (See FIG. 1). This causes the probing means 44 at the forward end of the arm 33 to move axially of the pipe 1.

The swinging of the probing means 44 in a horizontal plane is effected by the probing means swinging mechanism 35 (See FIG. 4). Upon the motor 36 being rendered operative, the rotation thereof is transmitted, through rotary shaft 37, bevel gears 38 and 41, rotary shaft 42 and ball joint 43, to the shaft 68, to thereby move the probing means 44 in swinging motion. The swinging movement of the probing means 44 increases the range of ultrasonic probing of the pipe 1 by the ultrasonic probing apparatus 2.

The angle of incidence of the ultrasonic sound waves incident on the surface of the pipe 1 can be varied by manipulating the probing means angle varying mechanism 62 (See FIG. 5). The rotation of motor 63 is transmitted, through the speed reducing means within the gear box 93, gears 64 and 65 and rotary shaft 66, to the gear 67. The rotation of gear 67 moves the arcuate guide plate 53 along the arcuate guide grooves 54 and 55, thereby causing the transmitter movable member 46 and receiver movable member 48 to move along the arcuate upper surfaces of the transmitter fixed member 47 and receiver fixed member 49 respectively in the direction of an arrow 92 in FIG. 7. Thus, the angle of incidence of the ultrasonic sound waves transmitted by the ultrasonic sound wave transmitter 50 with respect to the surface of the pipe 1 can be varied. The provision of a potentiometer 91 on the motor 63 (FIG. 5) permits the angle of incidence of ultrasonic sound waves to be obtained. A potentiometer, not shown, is mounted on each of the motors 20, 36 and 74, so that it is possible to detect the position of the probing means 44 circumferentially of the pipe 1, axially thereof and in the direction of swinging movement of the probing means 44. This permits the operator to accurately grasp the position on the pipe 1 in which ultrasonic probing is effected.

In the embodiment of the invention shown and described hereinabove, it is possible to scatter, circumferentially of the pipe 1, the motors 20, 36 and 74 and the transmission mechanism connected thereto of an ultrasonic probing apparatus in which the probing means 44 can be moved in swinging movement and can have its angle relative to a pipe to be probed to be varied, in addition to moving the probing means 44 in scanning movement circumferentially and axially of the pipe. Thus, the apparatus 2 can have its height markedly reduced. As a result, the ultrasonic probing apparatus 2 can be readily mounted around the pipe 1 even if the pipe 1 is disposed in an area where pipes are close together. Moreover, probing of the pipe can be effected without any trouble for detecting any flaws. The danger of exposing the operator to radiation can be avoided even if ultrasonic probing of pipes is carried out in an area where pipes are disposed close together.

Two circumferentially driving units 10 may be provided in place of one unit 10 and arranged in positions diametrically opposed to each other with respect to the center axis of the pipe 1. More specifically, the truck 83 may have mounted thereon a drive mechanism that is the same as the rotary shafts 15 and 19, the pair of support members 16, gears 17 and 18 and motor 20 which are mounted on the truck 11 of the circumferentially driving unit 10. By this arrangement, it is possible to balance the downwardly directed forces which are oriented in the direction of gravitational attraction and the upwardly directed forces which are against the direction of gravitational attraction, in an ultrasonic probing apparatus. This enables motors of low torque to be used in the two circumferentially driving units 10 and twisting of the units 10 and other troubles to be eliminated, thereby enabling the ultrasonic probing apparatus to be moved smoothly circumferentially of a pipe to be probed. Moreover, the rack 6 of guide rail 3 can be formed of a material of relatively low strength, such as a synthetic resinous material.

Also, the truck 83 may be eliminated and only the three trucks 11, 30 and 70 may be used to constitute an ultrasonic probing apparatus. When this is the case, the three trucks are preferably arranged at a 120 degree spacing from one another, to maintain the trucks balanced.

It will not be necessary to describe that the motors 20, 36 and 74 can be scattered circumferentially of the pipe 1 in the same manner as described with reference to the aforesaid embodiment, in an ultrasonic probing apparatus in which no probing means angle varying mechanism 62 is provided. In this case, the shaft 68 shown in FIG. 5 is directly attached to the upper surface of the casing 45.

In FIG. 2, the positions of the circumferentially driving unit 10 and axially driving unit 69 may be reversed.

Figure 8:
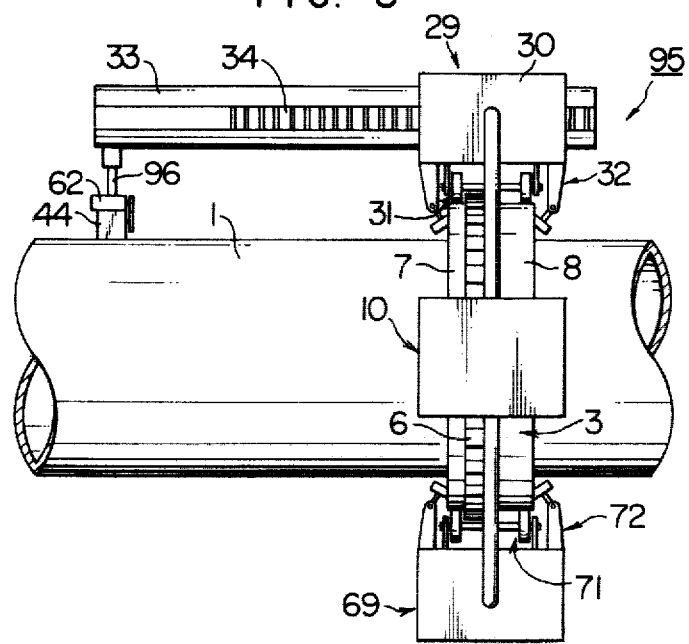
FIG. 8 is a side view of the ultrasonic probing apparatus comprising another embodiment of the invention.

FIG. 8 shows another embodiment in which parts similar to those shown in FIGS. 1 to 7 are designated by like reference characters. The ultrasonic probing apparatus 95 is similar in construction to the ultrasonic probing apparatus 2 except that the probing means swinging mechanism 35 of the latter is dispensed with. The arm 33 has attached to its forward end a support member 96 which supports a gear box of the probing means angle varying mechanism 62. The embodiment shown in FIG. 8 can achieve the same effects as the embodiment shown in FIGS. 1 to 7 except that the ultrasonic probing range is narrower because the probing means 44 cannot move in swinging motion.

The present invention permits the height of the ultrasonic probing apparatus to be markedly reduced as compared with similar apparatus of the prior art, thereby allowing ultrasonic probing of pipes to detect any flaws which might be present therein to be carried out readily without any trouble in an area where the pipes are arranged close to one another.

What is claimed is:

1. An ultrasonic probing apparatus comprising:
   annular guide rail means to be arranged in surrounding relation to a pipe to be ultrasonically probed for any flaws that might be present therein;
   a flaw detecting unit including a first truck mounted for circumferential movement on said rail means;
   a circumferentially driving unit including a second truck mounted for circumferential movement on said rail means; and
   an axially driving unit including a third truck mounted for circumferential movement on said rail means;
   said flaw detecting unit, said circumferentially driving unit and said axially driving unit being disposed separately from one another and arranged in spaced-apart relation on said annular guide rail means;
   means, separate from said rail means, for connecting said flaw detecting unit, said circumferentially driving unit and said axially driving unit together so that the trucks thereof may move together circumferentially of the pipe on the annular guide rail means and so that their weights produce torques about a horizontal pipe that generally cancel each other;
   said flaw detecting unit further including arm means movable axially relative to said annular guide rail means and said first truck and movable axially along the external surface of the pipe, and ultrasonic probing means for transmitting ultrasonic waves and receiving reflected waves from the pipe to detect pipe flaws and being attached to said arm means for movement therewith;
   said circumferentially driving unit further including first drive means for moving said circumferentially driving unit circumferentially of the pipe on said annular guide rail; and
   said axially driving unit further including second drive means, and transmission means for transmitting the drive force of said second drive means to said arm means to move said arm means axially of the pipe.

2. An ultrasonic probing apparatus as set forth in claim 1, further comprising swinging means for moving said ultrasonic flaw detecting means in swinging motion relative to said arm means.

3. An ultrasonic probing apparatus as set forth in claim 2, wherein said ultrasonic probing means comprises an ultrasonic sound wave transmitting section, and angle varying means for moving said ultrasonic sound wave transmitting section to vary the angle of incidence of ultrasonic sound waves incident on a surface of said pipe to be probed.

4. An ultrasonic probing apparatus as set forth in claim 1, wherein said circumferentially driving unit further includes a fourth truck mounted for circumferential movement in diametrically opposed position to said second truck on said annular guide rail means, said connecting means connecting all of said trucks to be symmetrically circumferentially spaced with respect to the center axis of said annular guide rail means, and said flaw detecting unit and said axially driving unit each being located between the two circumferentially driving unit trucks on said annular guide rail means.

5. An ultrasonic probing apparatus as set forth in any one of claims 1, 2, 3 and 4, wherein said transmission means is arranged in said connecting means.

6. An ultrasonic probing apparatus as set forth in claim 5, wherein each of said flaw detecting unit, said circumferentially driving unit and said axially driving unit trucks include wheels engaging said annular guide rail means and additional means in contact with said annular guide rail means for preventing rolling movement of each said unit about an axis aligned with its direction of movement on said annular guide rail means and parallel to a tangent to said annular guide rail means.

7. An ultrasonic probing apparatus comprising:
   annular guide rail means detachably mounted in enclosing relation around a pipe to be ultrasonically probed for any flaws that might be present therein and including a rack mounted on the outer periphery thereof;
   a flaw detecting unit, a circumferentially driving unit and an axially driving unit arranged on said annular guide rail means; and
   connecting means for connecting said flaw detecting means, said circumferentially driving means and said axially driving means together; wherein said flaw detecting unit comprises a first truck for movement on said annular guide rail means, arm means mounted on said first truck for movement axially of said pipe and having a second rack mounted thereon, ultrasonic flaw detecting means having a built-in ultrasonic sound wave transmitting section and attached to said arm means, swinging means attached to said arm means for moving said ultrasonic flaw detecting means in swinging motion, and angle varying means attached to said ultrasonic flaw detecting means for moving said ultrasonic sound wave transmitting section to vary the angle of incidence of ultrasonic sound waves incident on a surface to be probed of said pipe, said circumferentially driving unit comprises a second truck for movement on said annular guide rail means, a first motor mounted on said second truck, and a first gear supported by a first rotary shaft of said first motor and in meshing engagement with said first rack, said axially driving unit comprises a third truck for movement on said annular guide rail means, and a second motor mounted on said third truck, and said transmission mechanism comprises a second rotary shaft formed of resilient spring material connected to said second motor and arranged in said connecting means to extend into said first truck, and a second gear supported by said second rotary shaft and in meshing engagement with said second rack.

8. An ultrasonic probing apparatus as set forth in claim 7, wherein each of said first, second and third trucks include wheels engaging said annular guide rail means, and additionally have means attached thereto for preventing rolling movement about an axis aligned with its direction of movement on said annular guide means and parallel to a tangent to said annular guide rail means.

* * * * *